Figure 1:
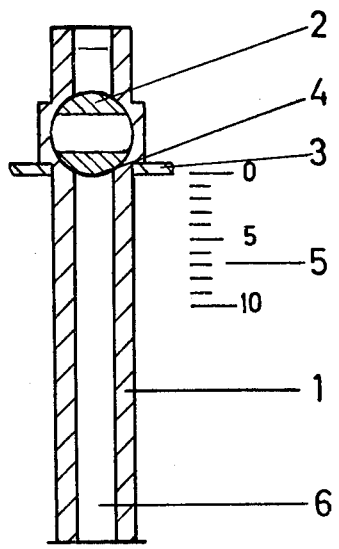

United States Patent [19]

Kirsch et al.

[11] 3,938,370
[45] Feb. 17, 1976

[54] DEVICE FOR MEASURING SEDIMENTATION RATES

[75] Inventors: Ulrich Kirsch, Melsungen; Wolfgang Buhler, Obermelsungen, both of Germany

[73] Assignee: Intermedicat GmbH, Lucerne, Switzerland

[22] Filed: Feb. 20, 1974

[21] Appl. No.: 444,107

[30] Foreign Application Priority Data

Feb. 28, 1973 Switzerland............. 2948/73

[52] U.S. Cl................ 73/61.4; 23/292; 73/426
[51] Int. Cl.²............................ G01N 15/04
[58] Field of Search............ 73/61.4, 61 R, 61.1 R, 73/426, 425.4 P; 23/292; 206/305, 459, DIG. 29; 215/230, 355; 233/26

[56] References Cited
UNITED STATES PATENTS

| | | | |
|---|---|---|---|
| 2,376,231 | 5/1945 | Cohn | 73/425.4 P |
| 2,649,245 | 8/1953 | Silverstolpe | 73/426 X |
| 2,741,913 | 4/1956 | Dovas | 73/61.4 |
| 3,091,124 | 5/1963 | Hindman | 73/425.4 P |
| 3,660,037 | 5/1972 | Sokol | 73/61.4 X |
| 3,734,079 | 5/1973 | Weber | 73/61.4 X |

FOREIGN PATENTS OR APPLICATIONS

| | | | |
|---|---|---|---|
| 525,505 | 5/1955 | Italy | 73/61.4 |
| 1,185,270 | 2/1959 | France | 73/425.4 P |
| 599,398 | 10/1959 | Italy | 73/61 R |

*Primary Examiner*—S. Clement Swisher
*Assistant Examiner*—Joseph W. Roskos
*Attorney, Agent, or Firm*—Curtis, Morris & Safford

[57] ABSTRACT

A device for facilitating rapid and accurate determination or measurement of sedimentation rates of fluid suspensions, e.g. erythrocytes in blood plasma, includes a sedimentation tube having open upper and lower ends, a scale with a zero point adjacent the upper end of the tube, and means for selectively opening and closing the tube adjacent said upper end, said means having a surface portion extending across the tube when the tube is closed, which surface portion is located precisely at the zero point in the scale.

9 Claims, 4 Drawing Figures

DEVICE FOR MEASURING SEDIMENTATION RATES

Determinations of blood-sedimentation rates are generally effected by the method of Westergren, wherein blood is injected or drawn into a transparent, graduated tube about 200 mm in length and having an open upper end. Generally, the sedimentation of the erythrocytes at the upper phase boundary can be checked after 1 and 2 hours. One disadvantage of this method is that the filling of the tube must be effected carefully so that the upper end of the blood column is precisely coincident with the zero mark of the graduation. This requires a certain skill and practice, especially when use is made of syringes of synthetic material and it is therefore difficult to avoid jerky movement of the pistons. Another disadvantage resides in the fact that small air bubbles gather at the upper end of the blood column only gradually and sometimes occupy several millimeters of the column. This makes an exact reading very difficult. For these reasons, blood sedimentation readings in the lower ranges are generally considered unreliable and only readings in the higher ranges are accepted as a diagnostic criteria.

In accordance with the present invention, a device is provided for adjusting the zero point quickly and exactly and, moreover, for eliminating completely the reading error caused by air bubbles.

Figure 2:
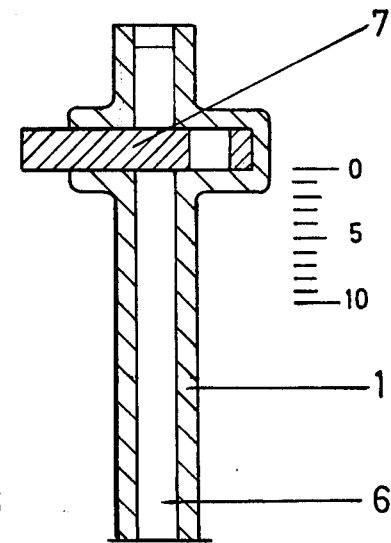
Figure 3:
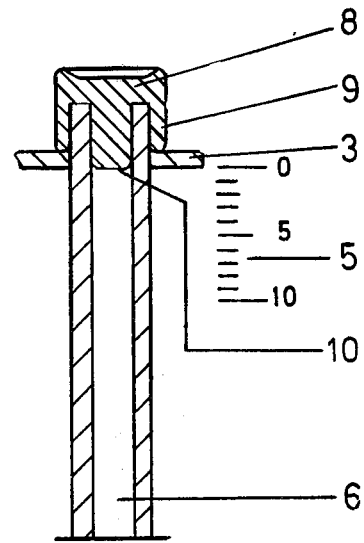
Figure 4:
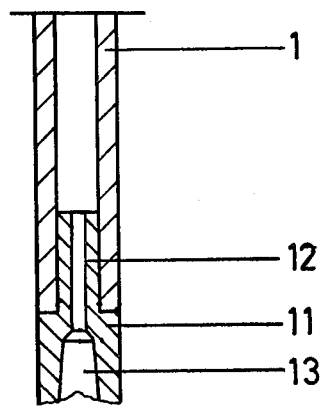

The device of the invention is illustrated by way of example in the accompanying drawing, in which:

FIGS. 1, 2 and 3 illustrate three embodiments of closure means for rapidly and precisely fixing a zero point from which measurement can be effected; and FIG. 4 illustrates a preferred embodiment of structure of the lower end of the device which may be used in conjunction with any of the closure means illustrated in FIGS. 1 to 3.

With reference now specifically to FIG. 1, an embodiment is shown which consists essentially of a transparent tube 1, preferably of glass or plastic, provided with a stopcock 2, a supporting flange 3 and a scale shown schematically at 5 with its zero point at the same level as the lowest portion of the periphery 4 of the stopcock 2.

The device shown in FIG. 2 is similar except for the fact that a sealing slide or gate valve 7 is provided in the upper end of the tube 1. The lower surface of the gate coincides with the zero point of the scale.

FIG. 3 shows an embodiment in which a stopper 8 with overhanging flange 9 is inserted into the upper end of the measuring tube 1. The lower and inner surface 10 of the stopper represents the zero mark which is brought to coincidence with the zero mark of the scale 5 by abutment of flange 9 with the top of supporting flange 3.

FIG. 4 shows an embodiment of the lower end of the measuring tube 1 provided with a stopper 11 having a capillary bore 12 and a conical recess 13 for reception of a syringe. It is to be understood, of course, that this embodiment is compatible with any of the structures illustrated in FIGS. 1, 2 and 3.

In operation, the tube 1 is filled with fluid 6, preferably from below, through the capillary 12 with a syringe inserted into the recess 13. When the tube 1 is filled completely, or at least to a level above the zero point on the scale 5, the upper end of the tube is sealed by turning the stopcock 2 to the closed position shown in FIG. 1, sliding the gate 7 to the closed position shown in FIG. 2, or inserting the stopper 8 to the closed position shown in FIG. 3. Withdrawal of the syringe, or even of the stopper 11 from the lower end of the tube 1, does not result in draining of the fluid from the tube and measurement of the sedimentation rate with the aid of the scale can begin without guesswork as to the precise upper level of the fluid. The tube can readily be placed in a suitable stand or rack with the stopper upward. The above-described manipulations require considerably less time than any methods usually employed in clinical practice for starting a blood sedimentation count. Moreover, in any case an exactly filled in blood column with an exactly defined zero point for the sedimentation count is insured.

When sealing devices having identical measurements are used for the determination of sedimentation rates, it is feasible to use a separate scale not marked on the blood sedimentation tube, the lower limit of the sealing device being the reference point for the zero point of the scale. In this case, the scale may be part of a mounting device or holder or it may be marked thereon.

Since the fluid column is prevented by atmospheric pressure from flowing out of the lower end of the tube, it is unnecessary to seal the tube at the lower end. However, when handled, mechanical vibrations may occur which may cause agitation and possibly disruption of the fluid column and, consequently, formation and rising of air bubbles. Therefore, it is preferable to reduce the diameter of the tube at the lower end sufficiently to eliminate this danger by the increase in surface tension thus attained. This is most desirably accomplished by inserting into the lower end of the tube a separate insert, such as that illustrated in FIG. 4, which has such a reduced inside diameter and also has an inner cone suitable for positioning a syringe.

The scale may be fixed to or marked on the tube. However, it may be more advantageous and is within the scope of the invention to have two scales fixed to or marked on the tube, the zero points of the scales being adjacent opposite ends of the tube and, in effect, making the tube double ended. With that embodiment, it is not necessary to pay attention to the direction in which the tube is filled.

We claim:

1. A sedimentation tube for use in measuring the sedimentation rates of erythrocytes in blood plasma, said tube having open upper and lower ends, a scale with a zero point adjacent the upper end of the tube and extending therefrom along the tube for use in determining said sedimentation rate; and means for selectively opening and closing said tube adjacent said upper end, said means having a surface portion extending across the tube when the tube is closed, which surface portion is located precisely at said zero point on the scale whereby filling of said tube with a liquid to said surface portion precisely locates the zero point of the column of liquid while said means allows the interior of the tube to be opened to the atmosphere to permit escape of air bubbles which may form in the tube between the column of liquid and said means during filling.

2. Sedimentation tube as defined in claim 1 wherein said closing means is a stopper fitting into the upper end of the tube.

3. Sedimentation tube as defined in claim 1 wherein said closing means is a rotatable stopcock.

4. Sedimentation tube as defined in claim 1 wherein said closing means is a slide valve.

5. Sedimentation tube as defined in claim 1 wherein said closing means is provided with a supporting flange adapted to be positioned outside and around the tube at the zero point when the closing means is in the operative closing position.

6. Sedimentation tube as defined in claim 1 provided at the lower end with an insert having a considerably reduced diameter.

7. Sedimentation tube as defined in claim 1 having two scales with zero points adjacent the opposite ends thereof.

8. A sedimentation tube ad defined in claim 1 wherein said scale is formed on the tube.

9. A sedimentation tube as defined in claim 6 wherein said insert has a central base formed therein including a first bore portion of predetermined uniform reduced diameter and a second bore portion on the extreme end thereof having a generally conical configuration for receiving the end of a syringe for filling the tube with blood through said insert.

* * * * *